US008920301B2

(12) United States Patent
Castillón Levano et al.

(10) Patent No.: US 8,920,301 B2
(45) Date of Patent: Dec. 30, 2014

(54) FULL NEONATAL CRITICAL CARE EQUIPMENT

(75) Inventors: Claudio Bruno Castillón Levano, Lima (PE); Carlos Andrés Mugruza Vassallo, Lima (PE); Jorge Luis Coello Durand, Lima (PE)

(73) Assignee: Pontificia Universidad Catolica Del Peru, Lima (PE)

( * ) Notice: Subject to any disclaimer, the term of this patent is extended or adjusted under 35 U.S.C. 154(b) by 263 days.

(21) Appl. No.: 13/259,724

(22) PCT Filed: Sep. 11, 2009

(86) PCT No.: PCT/IB2009/007014
§ 371 (c)(1),
(2), (4) Date: Apr. 26, 2012

(87) PCT Pub. No.: WO2011/030177
PCT Pub. Date: Mar. 17, 2011

(65) Prior Publication Data
US 2012/0220817 A1 Aug. 30, 2012

(51) Int. Cl.
*A61G 11/00* (2006.01)
*A61M 16/06* (2006.01)
*A61G 10/02* (2006.01)
*A61M 16/16* (2006.01)
*A61M 16/08* (2006.01)

(52) U.S. Cl.
CPC ............ *A61G 11/00* (2013.01); *A61M 2240/00* (2013.01); *A61M 16/16* (2013.01); *A61M 16/06* (2013.01); *A61G 2210/90* (2013.01); *A61G 11/007* (2013.01); *A61G 10/02* (2013.01); *A61M 16/0627* (2014.02); *A61M 16/0808* (2013.01)

USPC .............................................. 600/22; 600/21

(58) Field of Classification Search
CPC ... A61G 11/00; A61G 11/009; A61G 11/001; A61G 11/002; A61G 11/003; A61G 11/004; A61G 11/005; A61G 11/006; A61G 11/007; A61G 11/008; A61F 2007/0088; A61F 2007/0059; A61F 2007/006
USPC ......................................... 600/21–22; 5/603
See application file for complete search history.

(56) References Cited

U.S. PATENT DOCUMENTS 2,980,106 A * 4/1961 Carlson ........................... 600/22
4,321,913 A * 3/1982 Maluta et al. ................... 600/22
(Continued)

FOREIGN PATENT DOCUMENTS

EP          1380276 B1    3/2007
ES          2282589       10/2007

*Primary Examiner* — Jacqueline Cheng
*Assistant Examiner* — Eileen Foley
(74) *Attorney, Agent, or Firm* — Michael J. Brown

(57) ABSTRACT

Equipment for the comprehensive care of critical neonates that ventilates, incubates, monitors and facilitates medical procedures. This equipment includes a thermal ring keeping the neonatal bubble tempered, and that slides longitudinally through its axis to leave exposed the neonate during its care. The inside of the thermal ring includes circular heaters surrounding said ring. Inside the cabin there is a closed recipient with water that takes advantage of the heat of said bubble to humidify air passing through the inlet door and outlet pipeline, which carry humidified and hot air to neonate. Furthermore, the equipment includes a water container, open at its upper part and placed out of the bubble, that allows simultaneously limiting the gas pressure of inspiration and expiration and the gas pressure of the neonate through two pipes.

2 Claims, 7 Drawing Sheets

(56) References Cited

U.S. PATENT DOCUMENTS

| | | | |
|---|---|---|---|
| 4,481,938 A * | 11/1984 | Lindley | 601/43 |
| 6,884,211 B2 * | 4/2005 | Levano et al. | 600/22 |
| 2010/0168502 A1 * | 7/2010 | Delaporte et al. | 600/22 |
| 2011/0319702 A1 * | 12/2011 | Chilton, III | 600/22 |

* cited by examiner

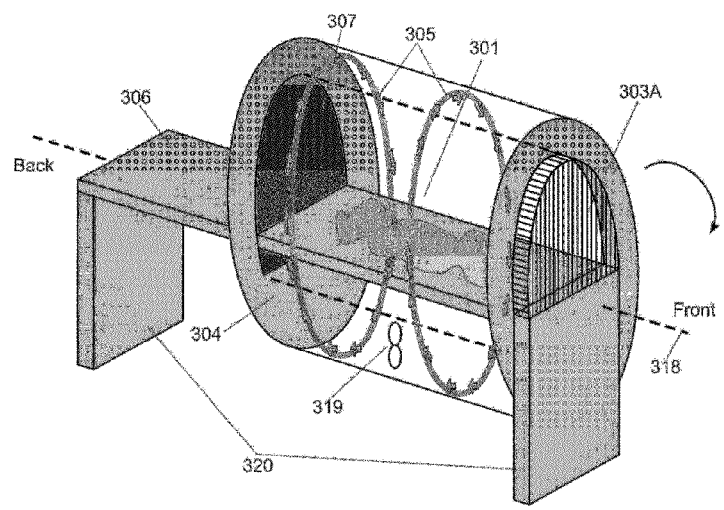
Figure 4A
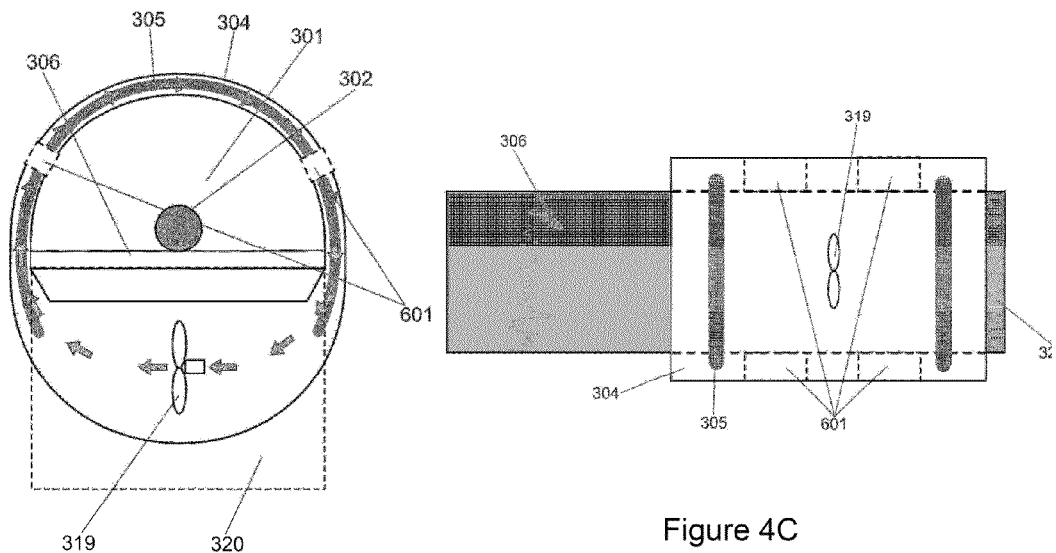
Figure 4C
Figure 4B

FULL NEONATAL CRITICAL CARE EQUIPMENT

TECHNICAL FIELD

This invention is a piece of medical equipment for use in the neonatal intensive care unit. More specifically, the equipment offers easy access and provides thermal ventilation therapy.

The invention solves five problems encountered in caring for newborns: uneven heating, lack of safety in the case of excess pressure during ventilation, slow access, excessive handling for endotracheal intubation, and condensation in the inhalation line tubes.

Currently, in order to care for newborn patients, Neonatal Intensive Care Units (NICUs) use different equipment, such as artificial respirators, incubators, air and oxygen mixers, and humidifiers, which result in a complex and costly operating system. These costs are further increased by the training required of medical professionals in the individual and collective handling of each one of these machines for the proper care of high-risk newborns. Furthermore, the individual pieces of equipment that make up the life support unit for high-risk newborns take up a great deal of space and a level of sterility that is difficult to maintain. As a consequence, the cost of running an NICU area is very high, which is reflected in the medical costs for high-risk newborns. Along with policy changes, this invention should help achieve costs lower than those in the United States, for instance, where costs per day run up to about US$1,000. Moreover, as the current system is made up of several separate pieces of equipment, any time there is a problem with one, the newborn ceases to receive comprehensive care, thus requiring the presence of medical personnel and a paramedic in the room at all times.

From a technical perspective, this group of separate pieces of equipment may put the newborn's life at risk due to possible unsafe connections, as well as an increased likelihood of human error by medical and paramedical personnel when using equipment with different functions and manufactured by different companies.

The fact that various pieces of equipment are involved and that hospitals may not always have all of the equipment at one time means that there is a deficiency in care. Furthermore, not all medical professionals are trained to use of multiple types of equipment.

In an endeavor to improve average-risk newborn care in hospitals, the Medical Equipment and Systems Research and Development Group (GIDEMS) of the Pontifical Catholic University of Peru (PUCP) developed: (1) The Neonatal Artificial Bubble (BAN), patented in the U.S. (U.S. Pat. No. 6,884,211) and Peru (PE000622-2002/OIN), which is made up of a closed circuit of warm air and a continuous ventilation circuit and has proven to have better functional characteristics than conventional incubators in the evenly spread propagation of heat, adaptation to uncontrolled intensive care environments, the duration of bacteria filters, lower noise level in the area containing the newborn, lesser probability of contamination between newborns, less heat loss, less oxygen consumption, etc. It also includes other benefits such as a sound player for the improved wellbeing of the newborn, an air and oxygen mixer and an improved humidification system. However, the BAN does not have a pulmonary ventilation circuit for newborns. (2) A bidirectional gas glow sensor, patented in the U.S. (U.S. Pat. No. 7,028,560) and Peru (PE000594-2002/01N); and (3) A Neonatal Bubble with an Air Channel Pressurizer, Peruvian patent application PE001492-2007/OIN, which possesses the benefits of the BAN, such as asepsis, a humidified environment, evenly-spread temperature and low operating noise, with the addition of a very significant function for the care of high-risk newborns: the control of parameters for the mixture of gases administered to the nostrils of the high-risk newborn, such as temperature and positive pressure.

This prototype also includes a bidirectional gas flow sensor developed by the GIDEMS. However, while the prototype pressurizes the air channels of the newborn, it does not control the pulmonary ventilation flow of the newborn.

Patent EP1529547 (2005) presents a piece of equipment that differs from conventional pulmonary ventilators in its portability, functioning as a supplement to incubators. Patent DE102006030520 (2008) of the Dräger company, has developed a control system for pulmonary ventilation that differs from the others only in its control algorithm, and also functions as a supplement to incubators. Finally, patent applications US2008125619 (2008), US200808081943 (2008) and US2008076962 (2008) contain the latest inventions in neonatal incubators, with the newest modifications to the state of the art, but do not incorporate the pulmonary ventilation function.

None of these inventions combines the pulmonary ventilation function with the incubation function. Additionally, all of them require the mobilization of the newborn for certain procedures, such as surgeries and intubations, etc.

INVENTION DISCLOSURE

The invention solves the underlying problems with the equipment used in the care of high-risk newborns. These problems may include: endotracheal intubation and resuscitation of the newborn, which are complicated procedures that normally require the newborn to be rotated 90° inside the bubble; destabilization of the pneumatic circuit due to the change in the position of the tubes during medical procedures; excess time needed to gain access to the newborn inside the incubator; and condensation of water vapor in the inhalation tubes that hinders ventilation due to the change in temperatures between the pulmonary ventilator, humidifier and incubator used in newborn care.

The equipment currently used in newborn care provide an open thermally-controlled environment, using a heater located under the cradle (U.S. Pat. No. 7,044,850) or a heater located in the upper part of the cradle (U.S. Pat. No. 6,616, 599). Therefore, in order to control the open neonatal environment with precision, it is necessary to use at least two heaters. Furthermore, an open environment depends on the environmental conditions of the NICU.

This equipment solves the intensive care support problems for high-risk newborns, such as ventilation, heating, humidification and mixture of air with oxygen to overcome life-threatening deficiencies during the first hours after birth.

The equipment supports the survival of high-risk newborns by providing them with warm, humidified, oxygen-enriched air in a sterile environment that may be remotely monitored in real-time. Thus, the essence of this invention may be described as "a piece of equipment that ventilates, tempers, humidifies, mixes air with oxygen and remotely monitors in real time."

This equipment for high-risk newborn care is comprised of the following elements:
  A thermal ring made up of two concentric cylinders with four side hatches, one or more heating elements between said cylinders, as well as a fan also between the cylinders.

A cradle that is fixed horizontally in one of the following ways:
  Held up by vertical supports on both ends, where part of the cradle is located inside the thermal ring
  Held up by a single vertical support connected to the front part, with the back sealed with a cover.
A bubble made up of a space enclosed on its underside by the cradle, at the top by the thermal ring, in front by the removable hatch and behind by the cover.
A Y connector connected to the newborn and used to receive the gas tubes.
A first water container, located outside the bubble, connected to a first inhalation tube coming from the Y connector, as well as a second exhalation tube from the Y connector, where the second tube is controlled by a second pneumatic action valve.
A second water container, located inside the bubble, connected to a third tube that comes from a gas mixture unit, and from which a fourth tube runs to the Y connector used for the ventilation of the newborn. This second container acts as a control element for the temperature and humidity of the outgoing gas flow directed toward the newborn.

It should be noted that this equipment also includes connection devices and tubes between the abovementioned components:
  A gas input connector for air or a low-pressure mixture of air and oxygen (at less than 1 PSI). This device is connected to a tube for input into the bubble.
  A gas storage device, with an input that allows for the continuous flow of gas, and an output connected to a tube that carries the mixed gas to a first activation valve.
  A first activation valve connected to the control unit, which in response to a signal from the control unit, permits or blocks the passage of the mixed gas flow to a flow sensor 2.
  A second activation valve, also connected to the control unit, which in response to a signal from the control unit, permits or blocks the passage of the gas flow exhaled by the newborn to the first water container.
  A flow sensor 2, connected to the control unit with an output connected to the pneumatic filter.
  A pneumatic filter, with an output connected to the second water container.
  Heating elements, which give off heat in the thermal ring in the direction of the cradle, ensuring a substantially constant temperature level.
  Sensors coupled to the tubes near the newborn that allow for the measurement of certain parameters of the gas (temperature, oxygen concentration and flow) the patient is receiving. These sensors are connected to the control unit.
  A first tube running from the Y connector to the first water container. The depth of the tube in the water determines the maximum positive pressure of the inhalation of the newborn.
  A second tube running from the Y connector to the first water container. The depth of the tube in the water determines the end-expiratory pressure of the newborn.

The inventive technical characteristics of the equipment are as follows:
  a. The heating elements on the thermal ring, located between the two concentric cylinders of the thermal ring, heat the air flow pumped by a fan located between the concentric cylinders.
  b. The thermal ring is adjustable and can be slid along the length of the neonatal bubble.
  c. A first water container connected to the bubble, which simultaneously limits the pressure of the gas for:
    inhalation, by way of a first tube with a maximum pressure determined by its depth (and which evacuates excess gas from the inhalation line); and
    exhalation of the newborn, by way of a second tube that has a minimum pressure determined by its depth for the evacuation of the gas coming from the exhalation line, maintaining a positive end-expiratory pressure
  d. A second water container, located inside the bubble, which uses the heat of the thermal ring to humidify the gas entering the second container by means of a third input tube, in order to subsequently conduct the humidified, heated air to the newborn through a fourth output tube from the second container.
  e. A gas storage tank, inside the thermal ring, which:
    Heats the gas mixture
    Attenuates or filters the oscillating pressure originating in the compressor
    Allows for the continuity of the gas flow delivered by the first activation valve The equipment for the comprehensive care of high-risk newborns comprises:
  A machine providing thermal and ventilation therapy
  A monitoring unit for receiving signals from the sensors connected to the newborn
  A control unit for receiving signals from the sensors and controlling the valves
  A gas mixture unit (air and oxygen mixture) connected to the control unit, which regulates the mixture of the gas flow delivered to a gas storage tank through a tube.

Below is an explanation of the equipment's systemic operation, taking into account the different ventilation, mechanical and thermo-pneumatic functions of the equipment.

Ventilation Function:
This function is comprised of the first water container that limits the inhalation and exhalation pressure of the newborn, and a second water container that humidifies the gas in the inhalation line. The function may be explained in three modes or times:
  1. Inhalation phase with excess pressure: Excess gas is evacuated through the regulation of the depth of the first tube, submerged in the first container. This regulation also determines the maximum inhalation pressure, normally instantaneously visualizing the inhalation pressure.
  2. Inhalation phase without excess pressure: The gas storage tank is maintained at a constant pressure through the compressor controlled by the control unit. The gas is then supplied to the second water container through a valve opened and closed (programmed frequency) by the control unit. The heated gas is humidified by the second water container, located inside the bubble, which makes use of the controlled temperature therein, before delivering the gas to the newborn.
  3. Exhalation phase: The positive pressure upon exhalation is simultaneously controlled and visualized through the regulation of the depth of a second tube.

Mechanical Function:
Quick and easy access to the newborn is provided by moving the cylindrical thermal ring along the axis of the ring and opening the main hatch, without the need to move the newborn while it continues to be connected to the ventilation system and other devices.

At the moment of performing thermal and ventilation therapy, access to the newborn shall only be through the hatches or openings used for hand maneuvering access of medical personnel, while the front part of the thermal ring is closed by the hatch and the fixed cover on the cradle surface.

Thermo-Pneumatic Function of the Invention's Heat Flow:

The fan is the source of an airflow that circulates over the heating elements and evens out the temperature of the ring.

In synthesis, the equipment for the comprehensive care of high-risk newborns performs three main functions, which are:

a) Control of the environmental temperature surrounding the newborn
b) Control of pressure, flow, humidity and temperature of the gas received by the newborn for mechanical ventilation
c) Provides easy and quick access for medical personnel to freely maneuver around the newborn, e.g. during an intubation procedure The equipment for the comprehensive care of high-risk newborns making up this invention solves the previously mentioned problems (see section on COMPREHENSION OF THE TECHNICAL PROBLEM) through the following advantages:

Allows for quick and easy access to the patient for the performance of emergency medical procedures such as endotracheal intubation, or during ventilation, without the need to rotate the newborn 90° in its cradle, even allowing for surgeries without removing the newborn from the cradle, since the thermal ring that encircles the surface of the cradle may be slid along the length of the bubble.

Allows for greater reliability of the mechanical ventilation process for the intubated newborn, since the tubes connecting the equipment to the newborn are fastened to the cradle and independent of the movement of the thermal ring.

Evens out the temperature inside the bubble using heating elements located inside the ring, which heat air flow that passes around them.

Reduces the risk of harm due to excess pressure on the newborn by way of a first tube submerged in the first water container, which evacuates excess gas from the inhalation line.

Allows for the accurate visualization (in cmH$_2$O) of the instantaneous pressure of the gas inhaled and exhaled by the newborn, through the tubes of the first water container, without the need for electronic visualization devices.

Avoids the condensation of the water in the tubes, through the location of a second water container (humidifier) inside the bubble and the tank inside the thermal ring, eliminating the temperature differences between the ventilation, humidification and incubation processes.

Reduces resistance to the gas flows in the inhalation line, since the inhalation line is much shorter due to its location inside the humidifier, closer to the newborn.

Simplifies monitoring of the newborn by using a single interface screen to visualize the incubation, pulmonary ventilation and vital sign monitoring processes.

Simplifies and facilitates assembly for manufacturing, maintenance and transportation.

Does away with check valves in the ventilation system.

(A) In the top figure, it may be observed that the inhalation pressure, specifically the peak pressure, may be visualized and controlled. For the inhalation phase, the first tube (309) submerged in the first water container (308) shows that the inhalation has not exceeded the maximum manometric inhalation pressure, and hence there is an air escape in this tube limiting the positive pressure of the inhalation line. The second tube (317) submerged in the first water container (308) ensures the positive manometric end-expiratory pressure. Inhalation with excess pressure prevented with the escape of gas through (309).

(B) In the middle figure, it may be observed that the peak inhalation pressure may be visualized and controlled. For the inhalation phase, the first tube (309) of the first water container (308) shows that the inhalation has not exceeded the maximum manometric inhalation pressure.

Inhalation through (312), (314) and visualization in (309).

(C) In the bottom figure, it may be observed that the exhalation pressure may be simultaneously controlled and visualized (when it is necessary to prevent the lungs (401) from collapsing) during the exhalation phase by way of a second tube (317).

Exhalation through (317).

Figure 1A:
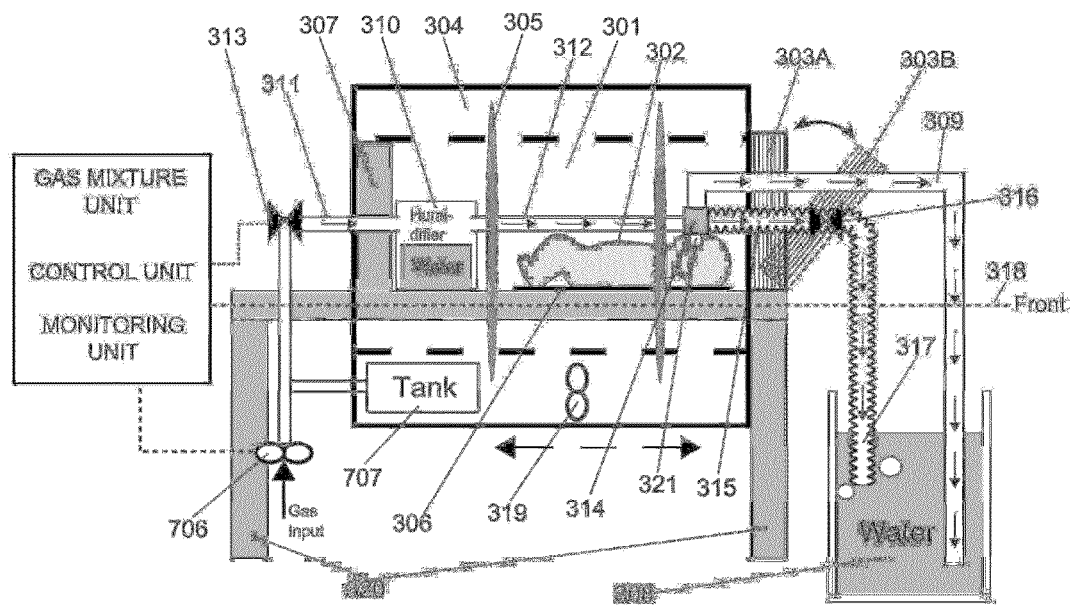
FIGS. 1A and 1B Basic diagram of two possible setups for the thermal-electric-pneumatic system, comprised of: heating elements (305) that encircle the inside of the thermal ring; a thermal ring (304), movable after opening a hatch (see dotted lines, 303B); first water container (308) that limits the inhalation and exhalation pressure of the newborn; and a second water container (310) that humidifies the gas (air and/or oxygen) in the inhalation line.
Figure 1B:
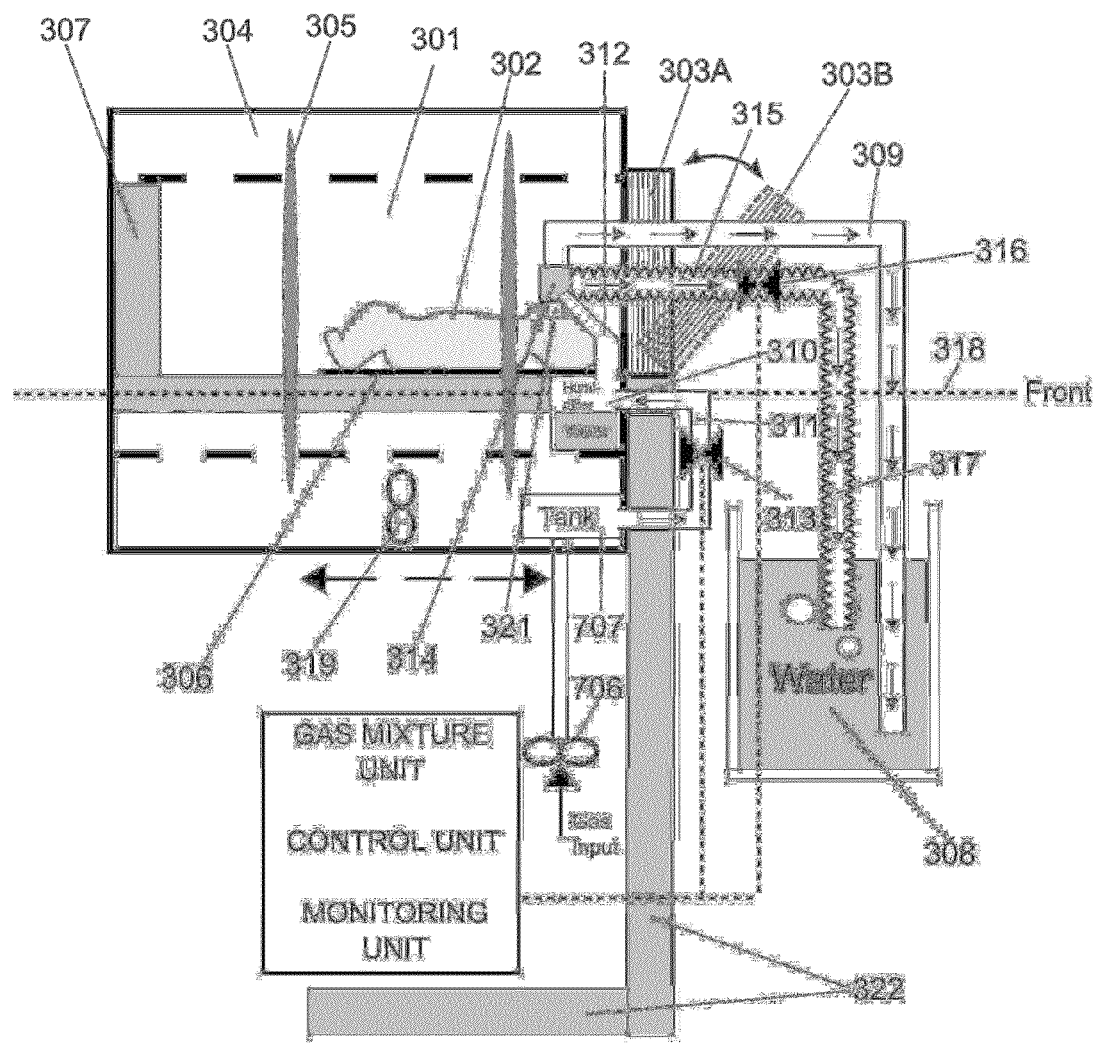
Figure 2A:
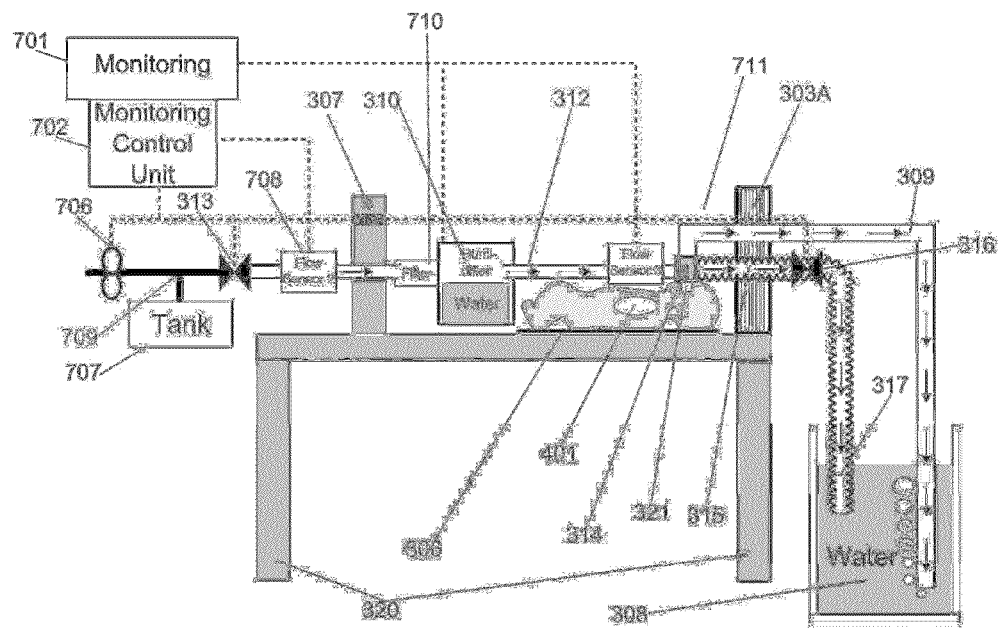
FIGS. 2A-2C Working diagrams of the electric-pneumatic system of the ventilation flow of the equipment, comprising: a first water container (308) that limits the inhalation and exhalation pressure of the newborn; and a second water container (310) that humidifies the gas in the inhalation line, which, together with the other elements, works as follows.
Figure 2B:
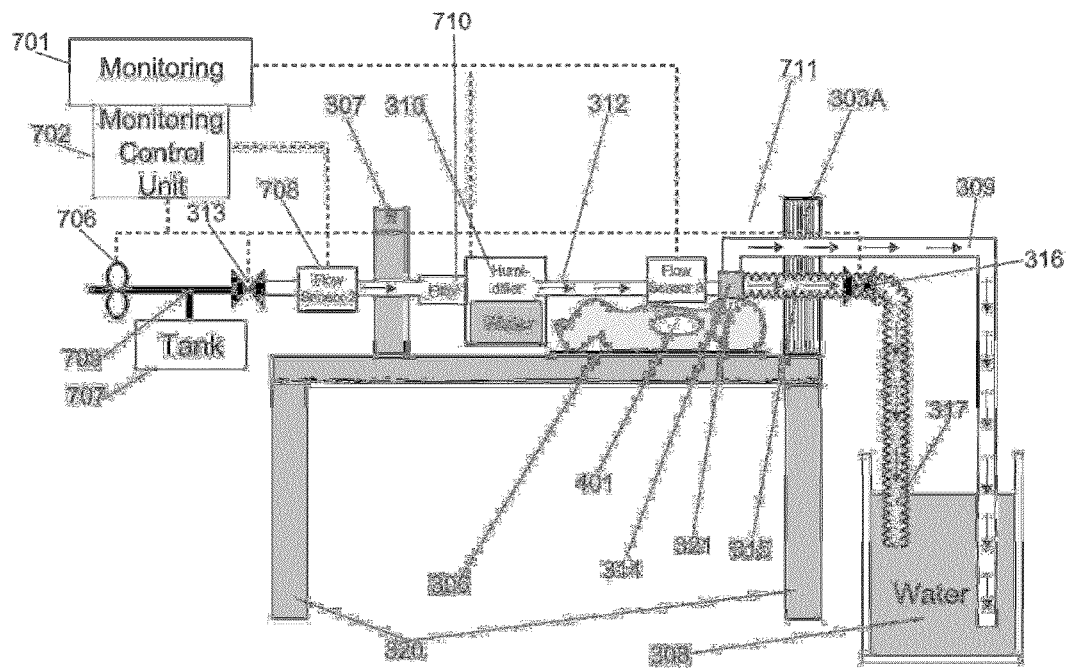
Figure 2C:
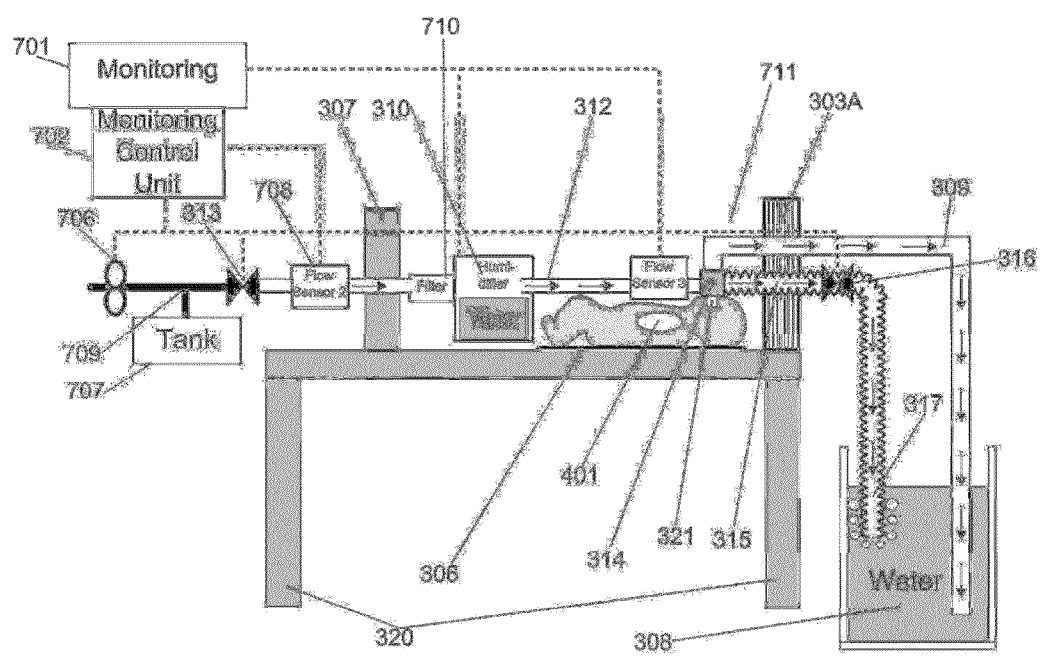
Figure 3A:
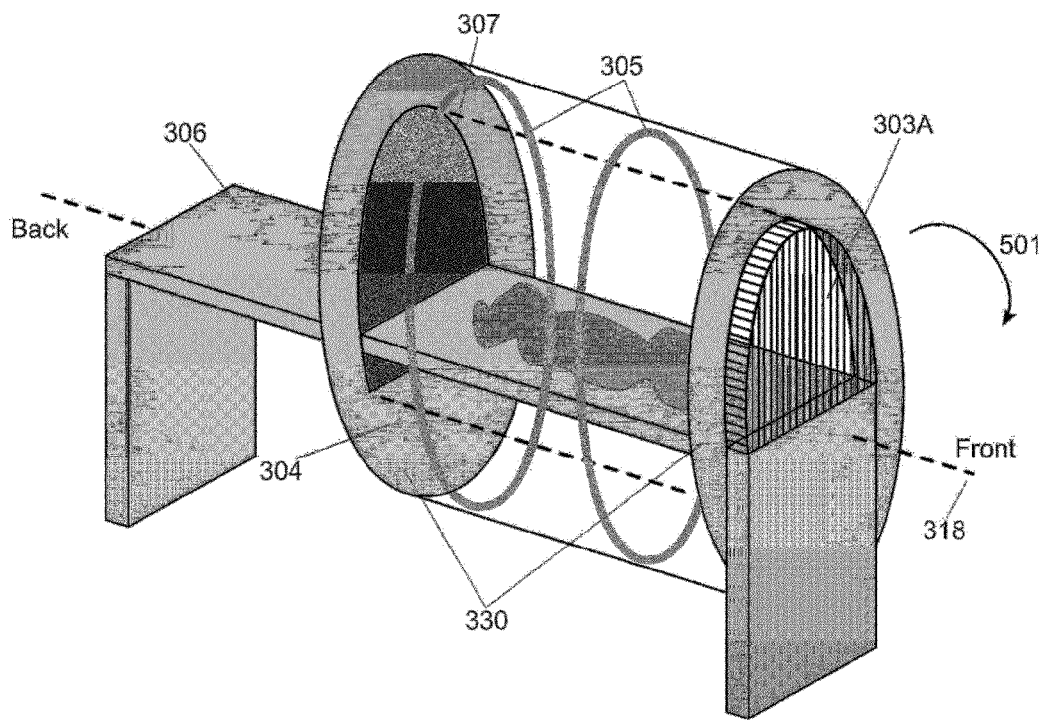
Figure 3B:
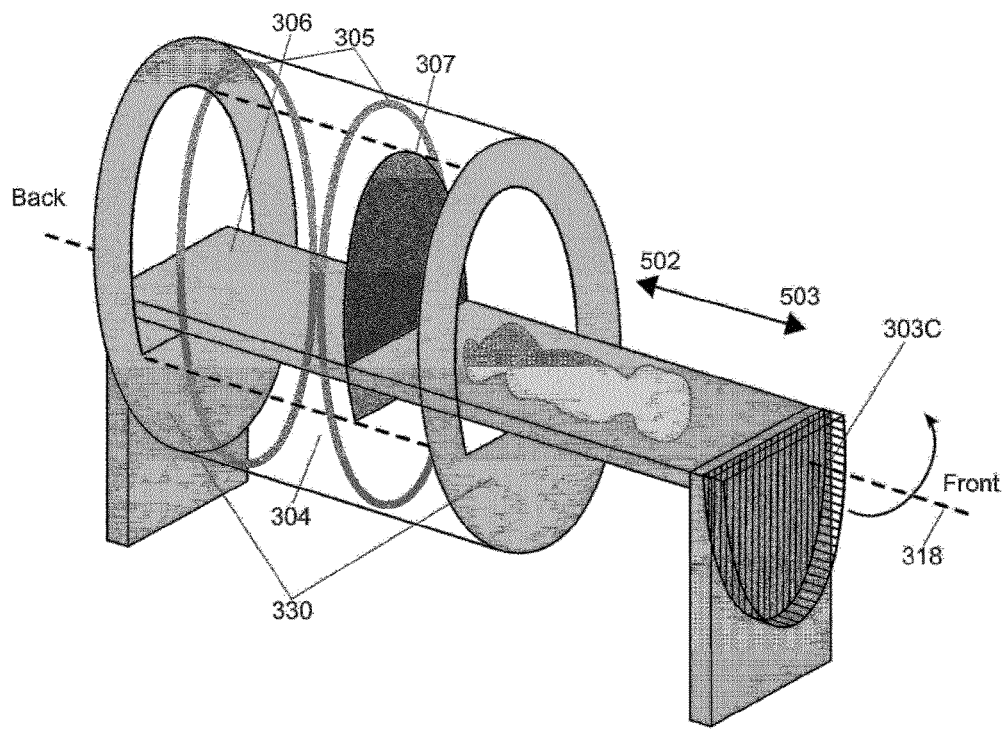

FIGS. 3A and 3B Working diagrams of the mechanics of the equipment and system proposed that explains one of the technical advantages of the invention, i.e. the access to the newborn through the movement of the cylindrical thermal ring along the ring axis (318) without the need to move the newborn, allowing for procedures to be performed on the newborn.

(A) In the top figure, the thermal ring is shown closed at its back part by a hatch thus allowing for the proper functioning of the heat therapy. This hatch may be opened (501) by moving it from its raised position (303A) to its lowered position (303C).

(B) The bottom figure shows the opened hatch and the moved thermal ring allowing for access to the newborn. This is achieved by moving the hatch (501) to its lowered position (303C) and sliding (502) the entire thermal ring (304). To return to the thermal therapy, the thermal ring must be slid back into its initial position (503) before raising the hatch (504) into its initial position.

FIGS. 4A-C (A) Thermo-pneumatic diagram of the invention's heat flow, in which the thermal ring has a fan (319) on its underside that acts as the source of the air flow that circulates over the heating elements and evens out the temperature of the ring. (B) This figure shows the hatches (601) with an angle designed to facilitate access to the newborn. The arrows indicate the airflow that is heated by the heating elements.

(C) This figure shows the hatches (601) that permit access to the newborn during thermal and/or ventilation therapy (not shown in the 3D figure).

Figure 5:
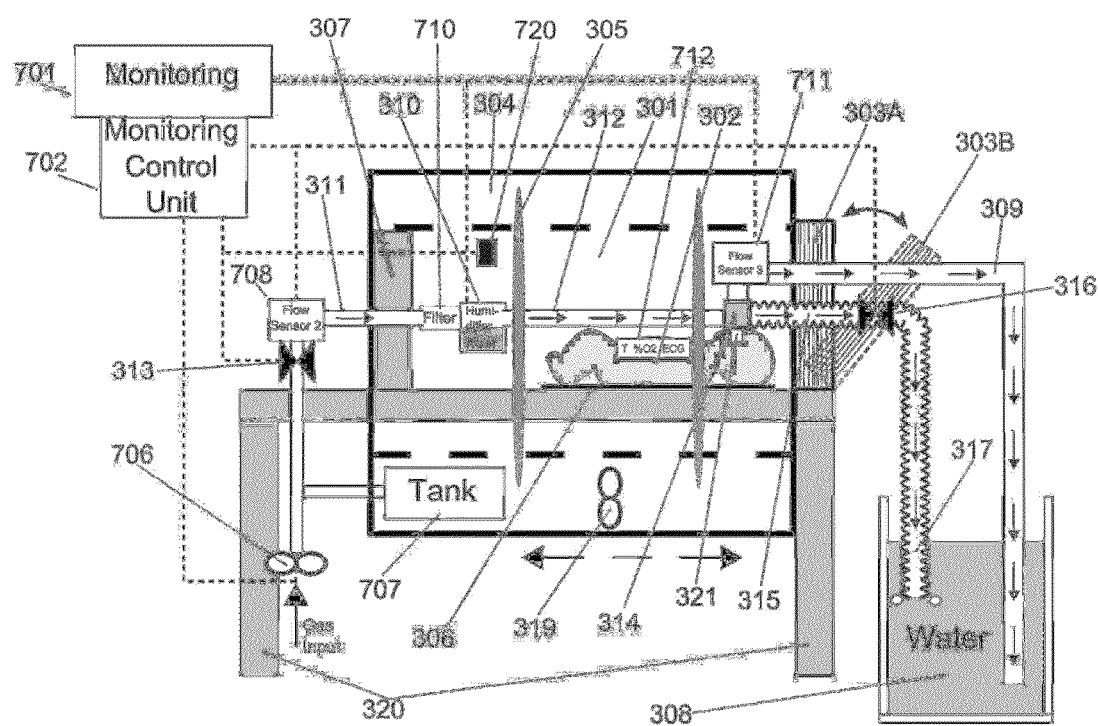
Figure 1A:
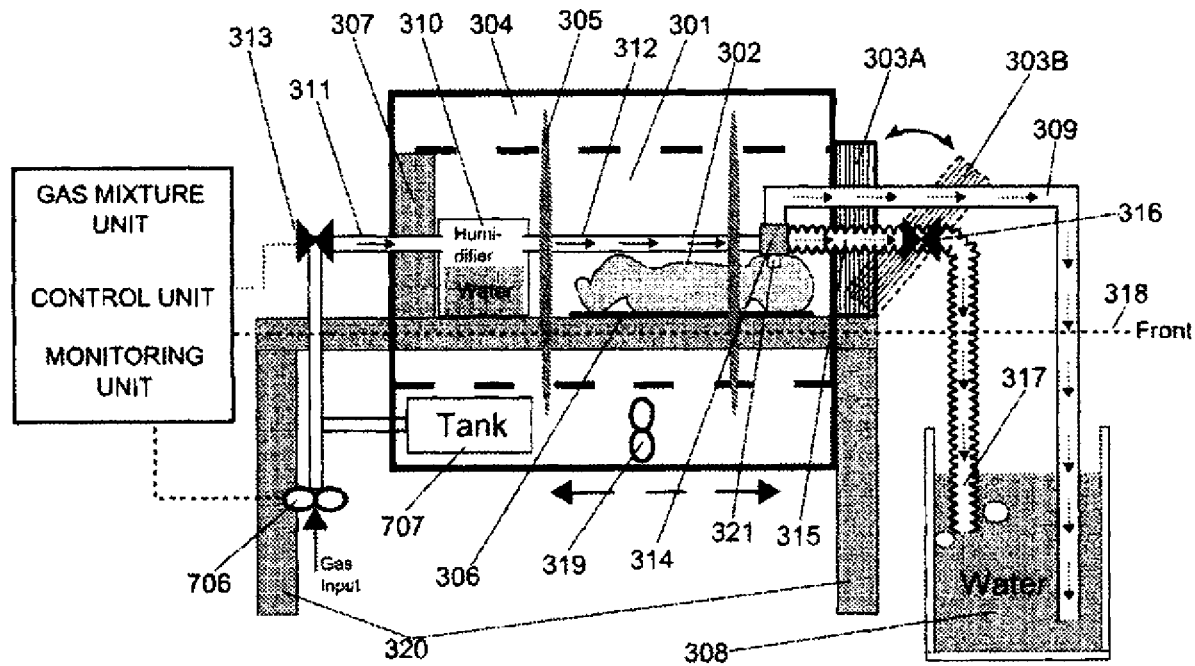
Figure 1B:
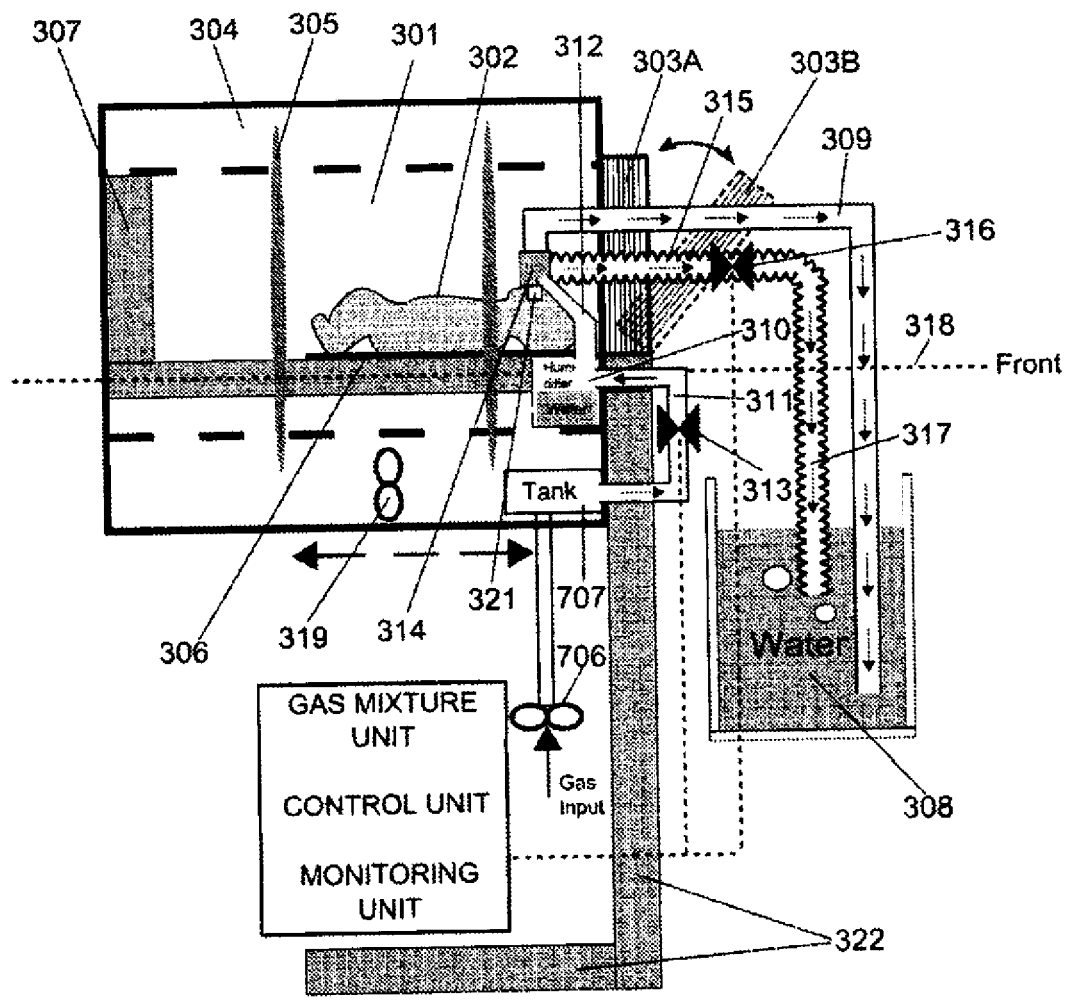
Figure 2A:
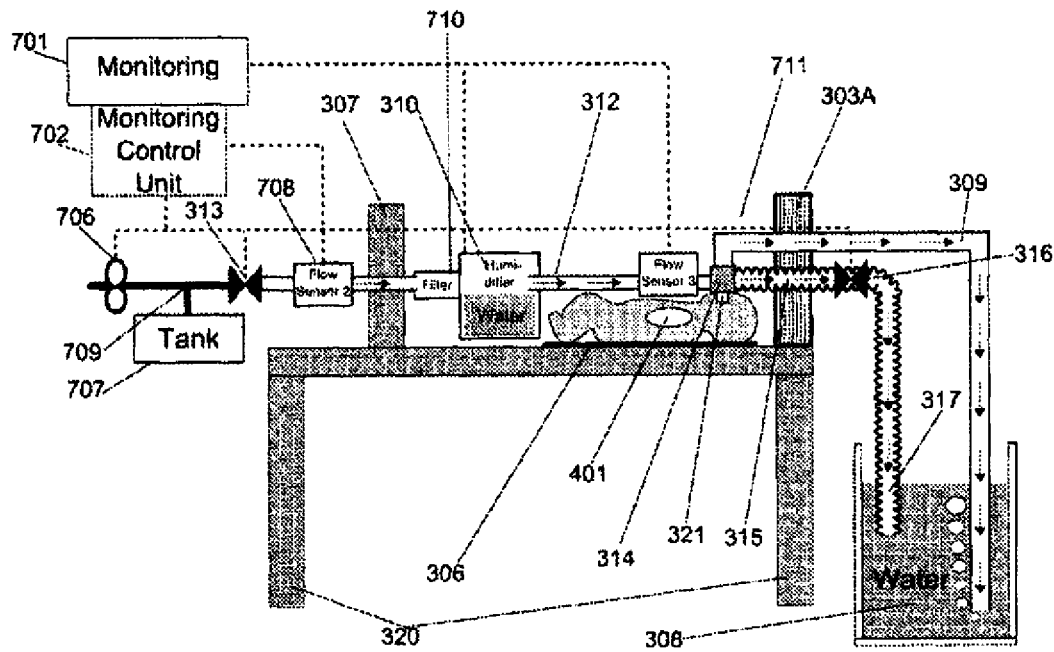
Figure 2B:
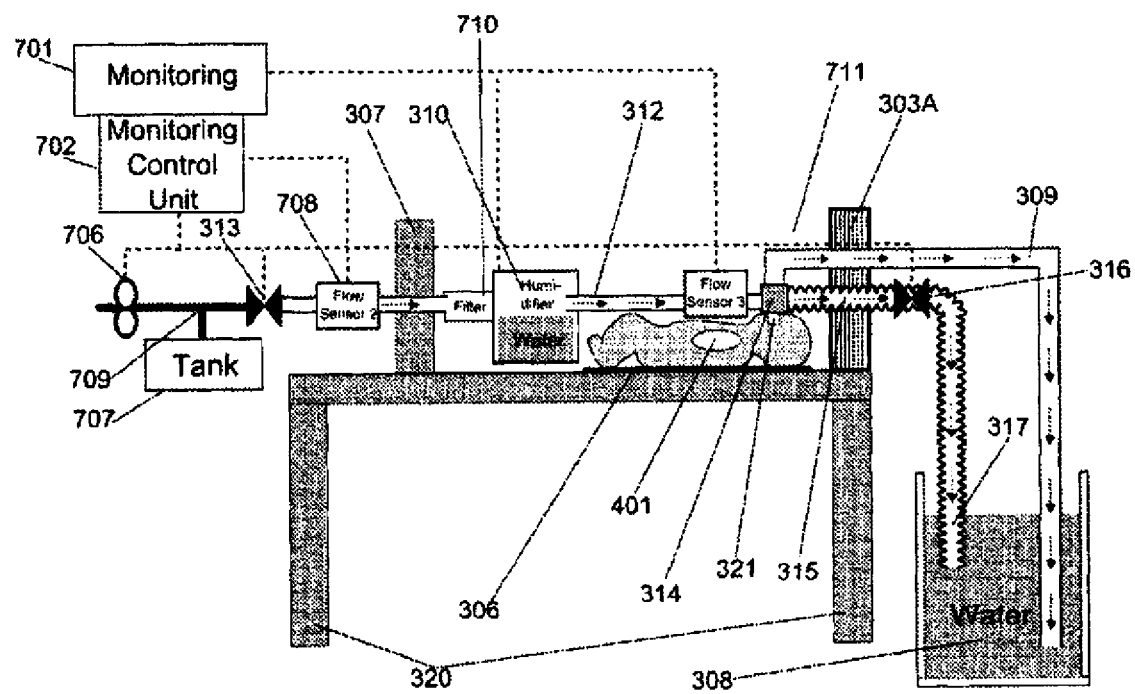
Figure 2C:
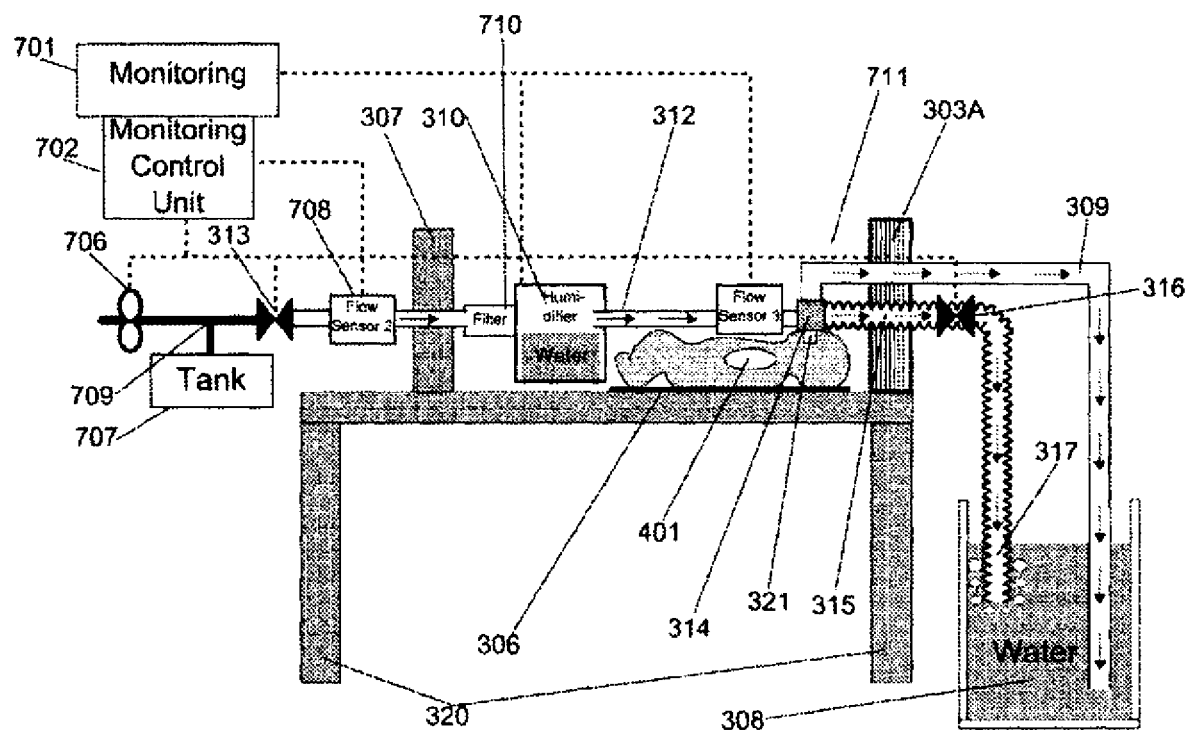
Figure 3A:
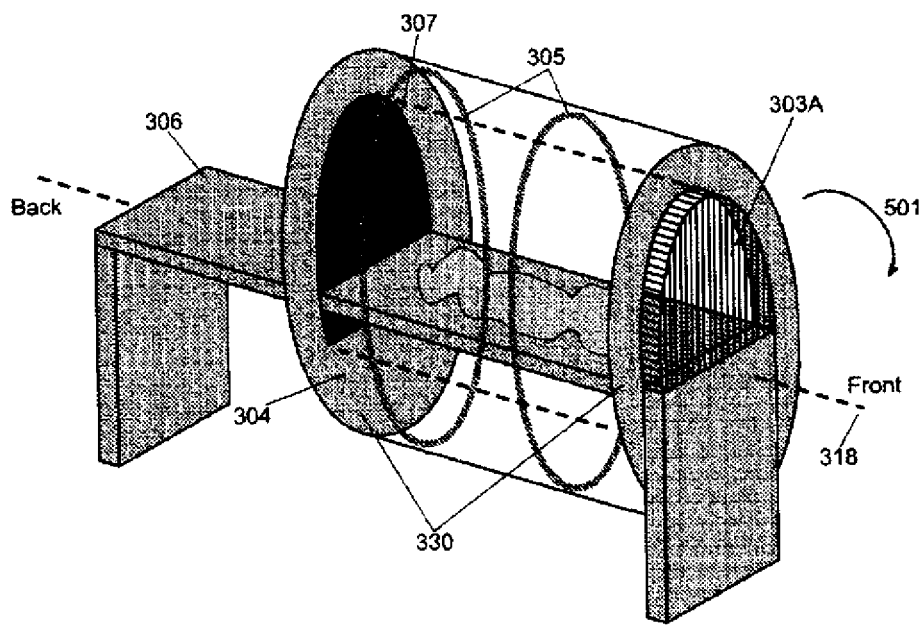
Figure 3B:
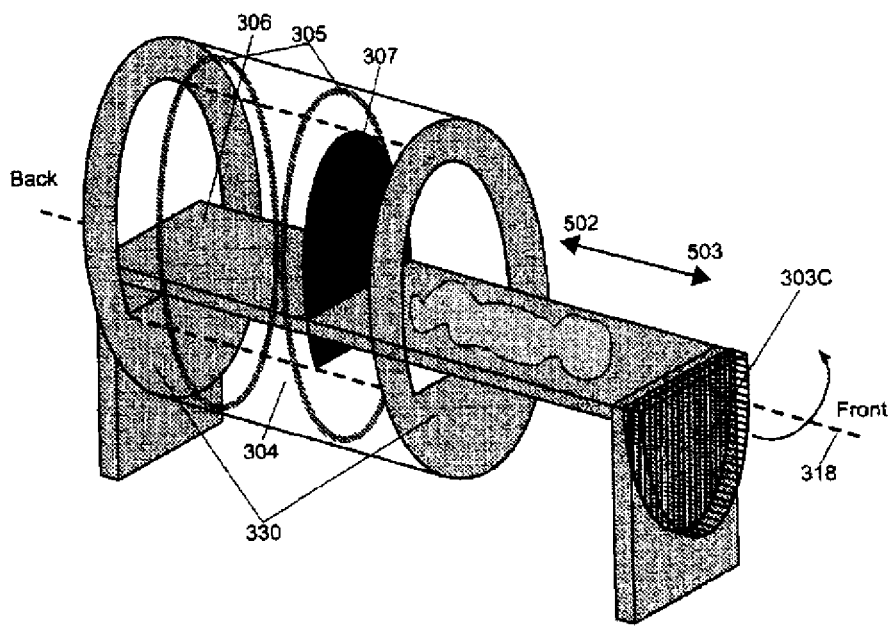
Figure 5:
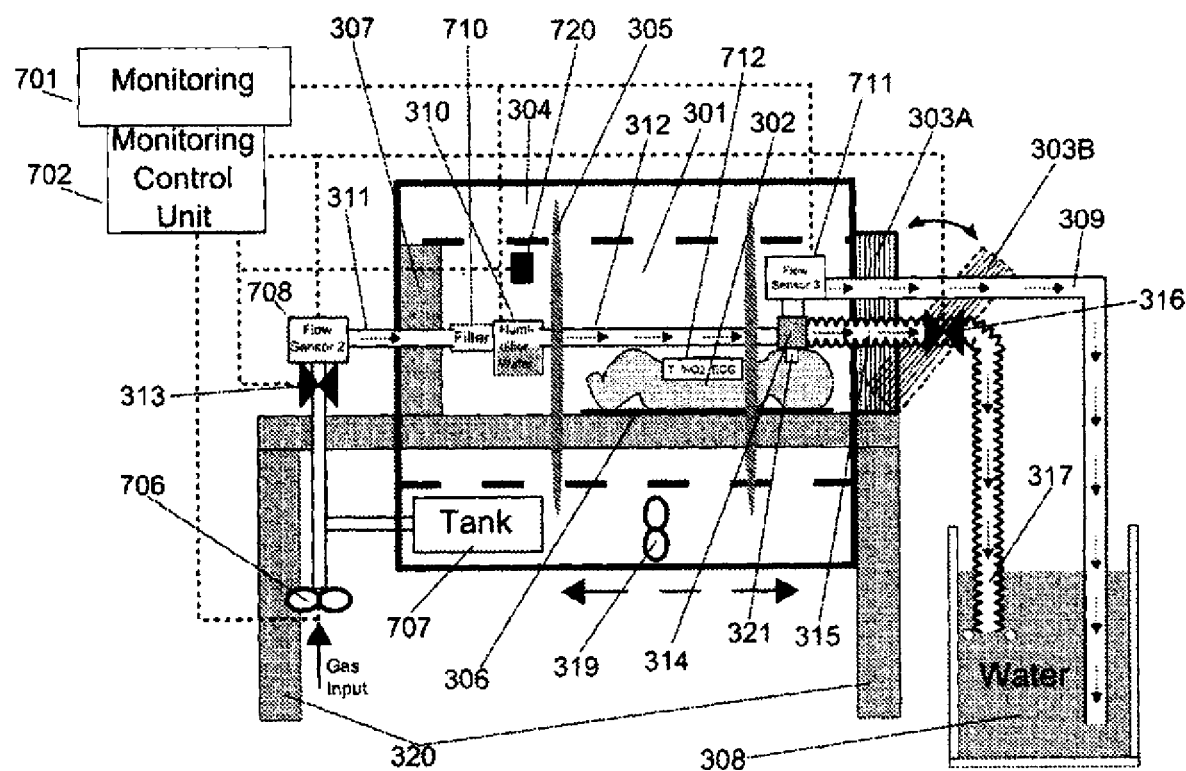

FIG. 5 Detailed diagram of the heating-electric-pneumatic equipment of the invention, which is comprised of: the thermal ring, which may be moved after opening a hatch (see dotted lines); a first container (308) that limits the inhalation and exhalation pressure; a second container (310) that humidifies the gas in the inhalation line; and a tank that heats the mixture of gases, attenuates or filters the oscillating pressure originating in the compressor and allows for the continuity of the gas flow delivered to the first electric valve.

PREFERRED METHODS TO DO THIS INVENTION

The following detailed explanation of the equipment shall be performed with the help of the graphic representations of the equipment for the comprehensive care of high-risk newborns. These graphic representations aid the correct understanding and clarity of the scope of this invention, its effects on the newborn and the technical benefits thereof.

FIG. 1 shows the main characteristics of the equipment for high-risk newborns that provides thermal therapy, ventilation therapy and the mixture of gases, in which said equipment is comprised of: a thermal ring (304) made up of two concentric cylinders with four side hatches, one or more heating elements (305) between said cylinders, as well as a fan (319) between the cylinders; a horizontal cradle (306), preferably rectangular; a hatch (303A, 303B); a cover (307); a first water container (308) on the external part of the equipment, which is fed by a first inhalation tube (309) and a second exhalation tube (317), both running to/from the Y connector (314), where the second tube is controlled by a second pneumatic action valve (316); a second water container (310) inside the bubble into which there runs a third exhalation tube (311) that exits from the gas mixture unit, and from which there exits a fourth tube (312) toward the Y connector (314) fastened to the newborn for ventilation—this container acts as a humidifier for the gas output flow directed toward the newborn (302); a bubble (301) consisting of a space limited on the bottom by the cradle (306), at the top by the thermal ring (304), to the front by the movable hatch (303A) and to the rear by the cover (307); and a gas storage tank (707) connected to the first pneumatic action valve (313).

The inventive technical characteristics of this equipment consist of the following:
   a. The heating elements (305), circular in shape, located between the two concentric cylinders of the thermal ring, heat the air flow pumped by a fan (319) located between the concentric cylinders.
   b. The thermal ring (304) is adjustable and can be slid along the length of the neonatal bubble (301).
   c. A first water container (308) on the outside of the bubble (301), which simultaneously limits the pressure of the inhalation gas for the newborn, by way of a first tube (309) with a maximum pressure determined by its depth for the evacuation of excess gas from the inhalation line; and the pressure of the exhalation gas for the newborn, by way of a second tube (317) that has a minimum pressure determined by its depth for the evacuation of the gas coming from the exhalation line, maintaining the positive end-expiratory pressure of the newborn.
   d. A second water container (310) located inside the bubble (301), which uses the heat of the thermal ring to humidify the gas entering by means of a third input tube (311) (said tube must be able to filter bacteria to be separated from the equipment, as will be shown in the detailed description below of FIG. 7), in order to subsequently conduct the humidified, heated air to the newborn (302) through a fourth output tube (312).
   e. A gas storage tank (707) inside the thermal ring, with a single input and output, which heats the gas mixture, attenuates or filters the oscillating pressure originating in the compressor and allows for the continuity of the gas flow delivered by the first electric activation valve.

It should be specified that the horizontal cradle may be held in that position in one of the following two ways:
   By vertical supports (320) on both ends, where part of the cradle is inside the cylindrical thermal ring (see top figure in FIG. 3), or
   By a single vertical support (322) connected to the front, with the back sealed with a cover (see bottom figure of FIG. 3).

The first (309), second (317), third (311) and fourth (312) tubes, as well as the valves (313, 316) that connect the two water containers (308, 310) attached to the cradle and the vertical support(s), are shown schematically in all of the Illustrations.

FIG. 2 shows the functioning of the ventilation therapy of the equipment, which may be explained in three situations:
   FIG. 2A shows how the peak pressure of inhalation with excess pressure may be visualized and controlled. The first tube (309) submerged in the first water container (308) shows that the inhalation has not exceeded the predetermined maximum manometric inhalation pressure (the gas that passes through the first tube reaches the maximum pressure level determined by the depth of the tube), hence there is an air escape in this tube, limiting the positive pressure of the inhalation line as a safety measure. This figure also shows how the lungs (401) of the newborn reach a maximum pressure level predetermined by the depth of the first tube (309) and the gas is evacuated in the bubbles that rise to the surface.
   FIG. 2B shows the case of inhalation without excess pressure. The compressor (706) controlled by the control unit (702) maintains a constant pressure in the gas storage tank (707). A valve, which is opened and closed by the control unit, provides gas to the second water container (310). The second water container (310), located inside the bubble, uses the controlled temperature in the bubble to humidify the heated gas for subsequent delivery to the newborn. Thus, it is possible to instantaneously control and visualize pressure of the inhalation phase, in which the first tube (309) of the first water container (308) shows that the inhalation has not exceeded the predetermined maximum manometric inhalation pressure. This also makes it possible to observe that the lungs (401) of the newborn do not have problems with the maximum inhalation pressure (the gas that passes through the first tube reaches the maximum pressure level determined by the depth of the tube) and the inhalation gas is conducted to the newborn without problems of excess pressure.
   FIG. 2C shows the case of exhalation, where the regulation of the depth of a second tube (317) simultaneously controls and visualizes the exhalation pressure when it is necessary to prevent the lungs (401) from collapsing (positive pressure at the end of exhalation defined by the depth of the second tube).

FIG. 3 consists of a working diagram of the mechanics of the equipment, showing the quick and easy access for the performance of medical procedures on the newborn without the need to move it, where the cylindrical thermal ring (304) may be slid along its axis (318), which is the same length as the cradle, from front to back and vice versa, along the entire length of the bubble. Both figures in FIG. 3 show the two concentric hollow cylinders joined on their ends by an annular sheet (330), made up of a hollow, ring-shaped cylinder, inside which there are circular heaters (305) and a fan (319, FIG. 4). This displays the basic makeup of the thermal ring (304) that encircles part (the front, if thermal therapy is being provided) of the longitudinal surface of the cradle (306). This thermal ring has a cover (307), and a movable hatch (303) on the vertical front surface, thus making up the bubble (302, FIG. 4) to house the newborn. Note that the cover (307) may be set up as follows:

Attached to the cradle, so that it remains in place when the thermal ring is moved (see FIG. 5)

Attached to the thermal ring, so that it moves together with the ring

The top figure of FIG. 3 shows the thermal ring (304) closed on its back side by the cover (307) and on the front by the hatch (303) shown in its vertical position (303A), thus allowing for the proper functioning of the heating system, where the hatch may be opened by moving it from the vertical position (303A) to its lowered position (303C).

The bottom figure of FIG. 3 shows the hatch in its lowered position (303C), permitting only the movement (502) of the thermal ring (304) permitting rapid access to the newborn (in this case, the thermal system has no effect on the newborn). After the medical personnel has performed the necessary procedure, the thermal ring is returned (503) to its initial position and the hatch is raised (504) into its vertical position.

Note that the lengthwise movement of the thermal ring (304) affects the control of the thermal system on the bubble, and thus on the newborn. However, this setup provides a significant advantage, in that the newborn is kept in the same position in the cradle, without moving the elements that make up the mechanical ventilation system, so that the ventilation therapy does not need to be interrupted.

In FIG. 4, Figures A, B and C show a thermo-pneumatic diagram of the invention. There is a fan (319) on the inside bottom part of the thermal ring (304), which is the source of the gas (air) flow that circulates through the heating elements (305, located between the two concentric cylinders of the thermal ring) that evens out the temperature of the air circulating inside the ring.

The cross section of Figure B shows the hatches (601) placed at an angle that ease access to the newborn, ensuring the comfortable positioning of the arms and elbows of medical personnel. The arrows inside the ring indicate the propagation of the hot air flow driven by the fan (319) and the two heating elements (305). Note that the thermal ring is designed to control the temperature of the bubble (302). Therefore, the inside cylinder of the ring is not necessarily circular in shape on the bottom part, since the dimensions of the fan may exceed the space between the two cylinders of the ring.

FIG. 5 shows a thermal-electric-pneumatic diagram of the invention equipment, which simultaneously provides incubation and pulmonary ventilation, as well as easy access to medical personnel in order to freely maneuver the newborn during medical procedures. The figure shows:

A bubble (301) consisting of a space enclosed on the bottom by the horizontal cradle (306), at the top by the thermal ring (304), to the rear by the cover (307) attached to the cradle, and to the front by the movable hatch (showed in its positions 303A and 303B).

A monitoring unit (701) for the visualization of parameters:
  a) Of the equipment: gas pressure and flow (711) and temperature (720) of the bubble
  b) Of the newborn: temperature, $O_2$ saturation in the blood, and the signal from the electrocardiogram electrodes (712)

A control unit (702) that gathers the signals from: the flow sensors (708), gas pressure sensors (711) and bubble temperature (720); and controls the action valves (316, 313) and heating elements (305);

Two arc-shaped heating elements (305) located inside the thermal ring. These elements give off heat from the thermal ring in the direction of the cradle, ensuring an essentially constant heat level inside the bubble.

A gas compressor (706) run by the control unit (702), which controls the gas stored in the tank (707) of the inhalation line. This inhalation line may use air from the surrounding environment or a mixture of air and oxygen from an external gas mixing unit.

A gas storage tank (707) inside the thermal ring, with a single input and output, which fulfills the following functions:
  a. Heats the gas mixture
  b. Attenuates or filters the oscillating pressure originating in the compressor
  c. Allows for the continuity of the gas flow delivered to the first electric action valve A first action valve (313), controlled by an electric signal coming from the control unit (702), which permits or blocks the passage of the gas mixture flow toward the flow sensor 2 (708).

A second flow sensor (708), connected to a control unit (702) which gas output is connected by means of a third tube (311) to a bacteria filter (710)

A bacteria filter (710) allows for the required level of asepsis to be maintained in the bubble. The output is connected to a second water container (310).

A second water container (310) located inside the bubble functions as a humidifier that humidifies and maintains the temperature of the gas flow directed toward the newborn through a fourth tube (312).

A first tube (309) runs toward the first water container, where the depth of the tube in the water determines the maximum positive pressure of inhalation of the newborn, known as positive end-inhalation pressure.

A second tube (317) runs toward the first water container where the depth of the tube in the water determines the minimum positive pressure of exhalation of the newborn, known as positive end-exhalation pressure.

A first water container (308) outside the bubble, fed by a first inhalation tube and a second exhalation tube coming from a Y connector (314). This second tube is controlled by the second pneumatic action valve (316).

A first activation valve (316) controlled by an electric signal coming from the control unit (702), which permits or blocks the passage of the flow through the tube (315) toward the second tube (317) for the exhalation of the newborn.

The second tube may or may not be submerged in the first water container (308), as follows:
  a. When it is not submerged, the outgoing exhalation pressure interacts with the environmental pressure.
  b. When it is submerged in the first water container (308), the outgoing exhalation pressure is equal to the environmental atmospheric pressure plus the pressure level measured in $cmH_2O$ of the submerged portion of the second tube (317).

INDUSTRIAL APPLICATION

This invention is for use in the medical field. It may be used as a separate component of other equipment or applications, as required. Logically, the invention should not be understood as usable exclusively for thermal and ventilation therapy for high-risk newborns; it may also be used together with any system that allows for the incorporations of the means and procedures necessary for the invention. Thus, the elements and procedures described herein are subject to variation, provided that such variation does not involve any changes in the basic concept of the invention. Any time the words or phrases "includes," "made up of," "comprised of" or "featuring" and any variation thereof are used throughout this description of the invention and the subsequent claims, and these shall not be understood as implying the exclusion of other procedures or components.

The invention claimed is:

1. A machine for the comprehensive care of a high-risk newborn comprising:
    a thermal ring (304) made up of two concentric cylinders joined at an end by an annular sheet (330), wherein the thermal ring slides longitudinally along a neonatal bubble (301);
    a heating element (305), located between the two concentric cylinders of the thermal ring (304), encircling said thermal ring;
    a pneumatic assembly capable of ventilating the lungs of the high-risk newborn wherein:
    a control unit (702) gathers signals from sensors, and controls actuating devices comprising valves, a compressor (706) and a gas mixture unit;
    the gas mixture unit provides a gas mixture of air and oxygen at a determined manometric pressure to the compressor (706), where the control unit (702) regulates the gas mixture of air and oxygen input to said compressor (706);
    the compressor (706) establishes the gas mixture flow that inputs to a tube connected to a gas storage tank (707);
    the gas storage tank (707) having an output which is connected by a tube directing the gas mixture into a first activation valve (313);
    the first activation valve (313), that according to a signal coming from the control unit (702), allows or prevents the flow of the gas mixture into a first water container (310) located inside the neonatal bubble (301), humidifying the gas mixture, the first water container (310) having an output tube (312) directed to a Y-shaped connector that is simultaneously connected to the newborn's mouth and to an inhalation tube (309) and to another tube (315) that is connected with an exhalation tube (317) by a second activation valve (316);
    the inhalation tube (309) and the exhalation tube (317) are submerged in a second water container (308), located outside of the bubble (301) which simultaneously limits the pressure of the inhalation and exhalation gas of the newborn, through the inhalation tube (309) that has a pressure determined by its input depth in said container to evacuate the excessive gas from the inhalation tube (309), and the exhalation tube (317) having a pressure determined by its input depth in said container to evacuate the gas coming from the exhalation tube (317), maintaining a positive pressure at the end of the newborn exhalation.

2. The machine for the comprehensive care of high-risk newborns according to claim 1 further comprising:
    a flow sensor (708) connected to a tube (311) located prior to the compressor (706), where within said tube is also located a pneumatic filter (710) whose output is connected to the first water container (310).

* * * * *

UNITED STATES PATENT AND TRADEMARK OFFICE
CERTIFICATE OF CORRECTION

PATENT NO. : 8,920,301 B2
APPLICATION NO. : 13/259724
DATED : December 30, 2014
INVENTOR(S) : Claudio Bruno Castillon Levano, Carlos Andres Mugruza Vassallo and Jorge Luis Coello Durand It is certified that error appears in the above-identified patent and that said Letters Patent is hereby corrected as shown below:

Title page should be deleted and substitute therefor the attached title page.

In the Drawings

Delete Drawing Sheets 1-7 and substitute therefor the Drawing Sheets as shown on the attached pages.

Signed and Sealed this
Eighteenth Day of August, 2015

Michelle K. Lee
*Director of the United States Patent and Trademark Office*

(12) United States Patent
Castillón Levano et al.

(10) Patent No.: US 8,920,301 B2
(45) Date of Patent: Dec. 30, 2014

(54) FULL NEONATAL CRITICAL CARE EQUIPMENT

(75) Inventors: Claudio Bruno Castillón Levano, Lima (PE); Carlos Andrés Mugruza Vassallo, Lima (PE); Jorge Luis Coello Durand, Lima (PE)

(73) Assignee: Pontificia Universidad Catolica Del Peru, Lima (PE)

( * ) Notice: Subject to any disclaimer, the term of this patent is extended or adjusted under 35 U.S.C. 154(b) by 263 days.

(21) Appl. No.: 13/259,724

(22) PCT Filed: Sep. 11, 2009

(86) PCT No.: PCT/IB2009/007014
§ 371 (c)(1),
(2), (4) Date: Apr. 26, 2012

(87) PCT Pub. No.: WO2011/030177
PCT Pub. Date: Mar. 17, 2011

(65) Prior Publication Data
US 2012/0220817 A1  Aug. 30, 2012

(51) Int. Cl.
A61G 11/00   (2006.01)
A61M 16/06   (2006.01)
A61G 10/02   (2006.01)
A61M 16/16   (2006.01)
A61M 16/08   (2006.01)

(52) U.S. Cl.
CPC ............ A61G 11/00 (2013.01); A61M 2240/00 (2013.01); A61M 16/16 (2013.01); A61M 16/06 (2013.01); A61G 2210/90 (2013.01); A61G 11/007 (2013.01); A61G 10/02 (2013.01); A61M 16/0627 (2014.02); A61M 16/0808 (2013.01)

USPC .................................. 600/22; 600/21

(58) Field of Classification Search
CPC ... A61G 11/00; A61G 11/009; A61G 11/001; A61G 11/002; A61G 11/003; A61G 11/004; A61G 11/005; A61G 11/006; A61G 11/007; A61G 11/008; A61F 2007/0088; A61F 2007/0059; A61F 2007/006
USPC ............................ 600/21-22; 5/603
See application file for complete search history.

(56) References Cited

U.S. PATENT DOCUMENTS 2,980,106 A * 4/1961 Carlson .................. 600/22
4,321,913 A * 3/1982 Maluta et al. ............ 600/22
(Continued)

FOREIGN PATENT DOCUMENTS

EP    1380276 B1   3/2007
ES    2282589      10/2007

Primary Examiner — Jacqueline Cheng
Assistant Examiner — Eileen Foley
(74) Attorney, Agent, or Firm — Michael J. Brown

(57) ABSTRACT

Equipment for the comprehensive care of critical neonates that ventilates, incubates, monitors and facilitates medical procedures. This equipment includes a thermal ring keeping the neonatal bubble tempered, and that slides longitudinally through its axis to leave exposed the neonate during its care. The inside of the thermal ring includes circular heaters surrounding said ring. Inside the cabin there is a closed recipient with water that takes advantage of the heat of said bubble to humidify air passing through the inlet door and outlet pipeline, which carry humidified and hot air to neonate. Furthermore, the equipment includes a water container, open at its upper part and placed out of the bubble, that allows simultaneously limiting the gas pressure of inspiration and expiration and the gas pressure of the neonate through two pipes.

2 Claims, 7 Drawing Sheets

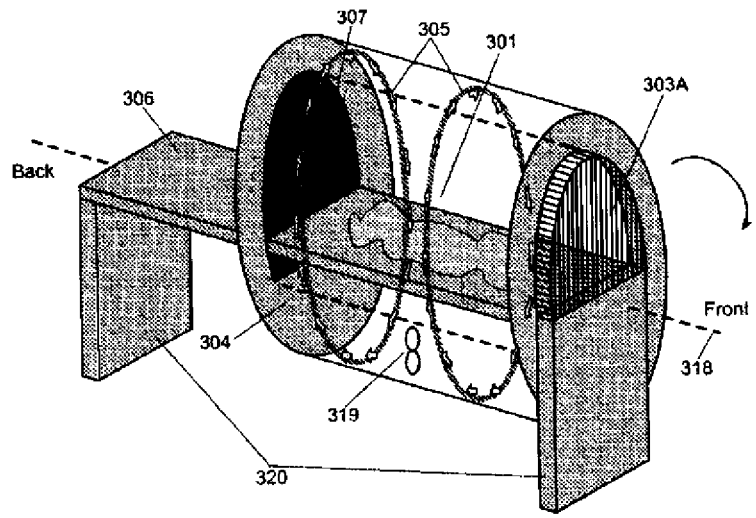
Figure 4A
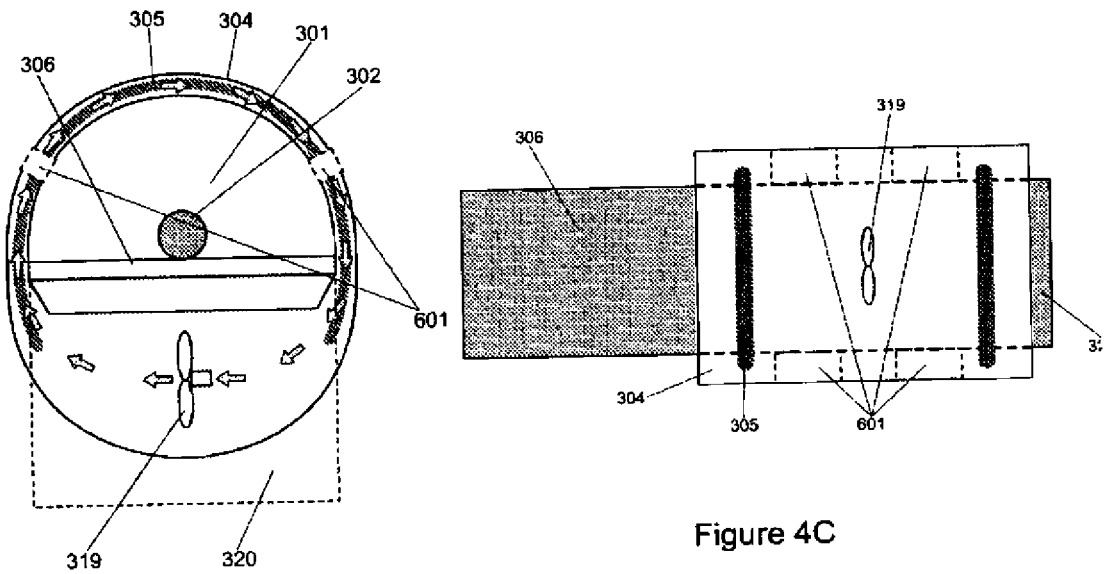
Figure 4B
Figure 4C